United States Patent
Jung et al.

(10) Patent No.: US 10,189,900 B2
(45) Date of Patent: Jan. 29, 2019

(54) METHOD FOR SCREENING FOR AUTOPHAGY ACTIVATOR OR INHIBITOR

(71) Applicants: KOREA FOOD RESEARCH INSTITUTE, Gyeonggi-do (KR); REGENTS OF THE UNIVERSITY OF MINNESOTA, Minneapolis, MN (US)

(72) Inventors: Chang Hwa Jung, Seoul (KR); Tae Youl Ha, Seoul (KR); Ji Yun Ahn, Gyeonggi-do (KR); Do Hyung Kim, Shoreview, MN (US); Ji Man Park, Minneapolis, MN (US)

(73) Assignees: KOREA FOOD RESEARCH INSTITUTE, Gyeongi-do (KR); REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 79 days.

(21) Appl. No.: 15/309,674

(22) PCT Filed: Jul. 2, 2014

(86) PCT No.: PCT/KR2014/005913
§ 371 (c)(1),
(2) Date: Nov. 8, 2016

(87) PCT Pub. No.: WO2015/170795
PCT Pub. Date: Nov. 12, 2015

(65) Prior Publication Data
US 2017/0226202 A1    Aug. 10, 2017

(30) Foreign Application Priority Data
May 8, 2014    (KR) .......... 10-2014-0054973

(51) Int. Cl.
*C07K 16/28*    (2006.01)
*G01N 33/68*    (2006.01)

(52) U.S. Cl.
CPC ......... *C07K 16/28* (2013.01); *G01N 33/6872* (2013.01); *C07K 2317/34* (2013.01); *C07K 2317/40* (2013.01); *G01N 33/6896* (2013.01); *G01N 2333/4703* (2013.01); *G01N 2510/00* (2013.01); *G01N 2800/70* (2013.01)

(58) Field of Classification Search
CPC ............... C07K 16/28; C07K 2317/40; C07K 2317/34; G01N 33/6872; G01N 2800/70; G01N 33/6896; G01N 2510/00; G01N 2334/4703
See application file for complete search history.

(56) References Cited

U.S. PATENT DOCUMENTS

| | | | |
|---|---|---|---|
| 5,858,669 A | 1/1999 | Levine | 435/6 |
| 6,432,914 B1 | 8/2002 | Levine | 514/2 |
| 2012/0258550 A1 | 10/2012 | Wu et al. | 436/501 |

FOREIGN PATENT DOCUMENTS

| | | | | |
|---|---|---|---|---|
| EP | 2383294 | | 11/2011 | C07K 16/18 |
| KR | 10-2012-0121754 | | 11/2012 | A61K 39/395 |

OTHER PUBLICATIONS

International Search Report (ISR) in PCT/KR2014/005913, dated Feb. 2, 2015 published in WO 2015/170795.
Kang, R., et al., (2011). "The beclin 1 network regulates autophagy and apoptosis". *Cell Death and Differentiation* 18(4):571-580.
Oppermann, F.S., et al., (2009). "Large-scale proteomics analysis of the human kinome". *Molecular & Cellular Proteomics* 8(7):1751-1764.
Wang, R.C., et al., (2012). "Akt-mediated regulation of autophagy and tumorigenesis through beclin 1 phosphorylation". *Science* 338(6109):956-959.

*Primary Examiner* — Ruixiang Li
(74) *Attorney, Agent, or Firm* — Harness, Dickey & Pierce, P.L.C.

(57) ABSTRACT

The present invention provides a method for screening for an autophagy activator or inhibitor comprising the steps of: (a) making a test material to be analyzed come into contact with cells containing Beclin 1 protein; and (b) analyzing the degree of phosphorylation at the $30^{th}$ serine amino acid residue of the Beclin 1 protein. The test material is determined to be an autophagy activator when the phosphorylation of the Beclin 1 protein is up-regulated, and the test material is determined to be an autophagy inhibitor when the phosphorylation of the Beclin 1 protein is down-regulated. The present invention first establishes, by ULK1, the mechanism of phosphorylation at the $30^{th}$ serine amino acid residue of Beclin 1.

5 Claims, 4 Drawing Sheets
Specification includes a Sequence Listing.

METHOD FOR SCREENING FOR AUTOPHAGY ACTIVATOR OR INHIBITOR

CROSS-REFERENCE TO RELATED APPLICATIONS

This application is a national phase application of PCT Application No. PCT/KR2014/005913, filed on Jul. 2, 2014, which claims the benefit and priority to Korean Patent Application No. 10-2014-0054973, filed May 8, 2014. The entire disclosures of the applications identified in this paragraph are incorporated herein by references.

FIELD

The present invention was made with the support of the Ministry of Science, ICT, and Future Planning of the Republic of Korea, under Project No. E0131601, which was conducted under the research project, entitled "Main Business of Korean Food Research Institute" within the project named "Pharmacokinetic study of Phytochemicals from Korean traditional foods" by the Korean Food Research Institute under the management of the Korean Food Research Institute, from 1 Jan. 2013 to 31 Dec. 2013.

The present invention relates to a method for screening an autophagy activator or inhibitor.

BACKGROUND ART

Autophagy is a system in which cells resupply intracellular nutrients by enclosing, in an environment that is deficient in intracellular nutrients, unnecessary proteins, aged small organs, and the like in membrane vacuoles composed of a lipid bilayer and then merging the same into lysosomes, thereby inducing the lysis of internal materials enclosed therein, and the Autophagy plays an important role in the maintenance of intracellular homeostasis. It is found that the autophagy plays an important role in controlling various human physiological and pathological states, such as cell growth, differentiation, metabolism, cancer, brain diseases, and immunity, and thus, the autophagy receives a lot of interest from the world. Autophagy may be subdivided into macroautophagy, microautophagy, and chaperone mediated autophagy (CMA) depending on the operation mechanism and function, and these three types of Autophagy are differently induced in individual forms while coexisting in cells. For example, autophagy occurs in even normal cell conditions, but macroautophagy is promptly induced in nutrient-deficient conditions. When stress is maintained for 6-8 h, macroautophagy is gradually decreased, and CAM induction occurs within 12-24 h. Autophagy is variously subdivided depending on the type of cargo: mitophagy for protecting cell damage by selectively removing damaged mitochondria, and ribophagy, reticulphagy, and pexophagy depending on the degradation of ribosomes, endoplasmic reticulum, and peroxisomes. In addition, macrolipophagy has recently been introduced, which is also involved in the direct degradation of intracellular lipid droplets generated by fatty acids. Although the functions of autophagy are found in various disease models and there is much interest therein, the accurate mechanisms thereof and the functions of involved molecules have not been well known so far.

As for patents relating to Beclin 1 involved in the autophagy mechanism, EP 2383294 discloses a technique of treating or diagnosing neurodegenerative diseases using antibodies specifically binding to Thr119 phosphorylated Beclin 1; U.S. Pat. No. 6,432,914 discloses a technique of treating cancer using Beclin 1 itself as a protein drug; and U.S. Pat. No. 5,858,669 discloses a technique of diagnosing cancer using Beclin 1 mutation.

Throughout the entire specification, many papers and patent documents are referenced and their citations are represented. The disclosure of the cited papers and patent documents are entirely incorporated by reference into the present specification, and the level of the technical field within which the present invention falls and the details of the present invention are explained more clearly.

DETAILED DESCRIPTION OF THE INVENTION

Technical Problem

The present inventors endeavored to develop a method for screening an autophagy activator or inhibitor capable of regulating autophagy that acts an important role in the maintenance of cellular homeostasis. As a result, the present inventors established that an autophagy activator or inhibitor can be screened by analyzing the degree of phosphorylation of the 30th amino acid residue serine of Beclin 1 protein, and thus completed the present invention.

An aspect of the present invention is to provide a method for screening an autophagy activator.

Another aspect of the present invention is to provide an antibody specifically binding to Beclin 1 protein with the 30th amino acid residue serine phosphorylated.

Other purposes and advantages of the present invention will become more obvious with the following detailed description of the invention, claims, and drawings.

Technical Solution

In accordance with an aspect of the present invention, there is provided a method for screening an autophagy activator or inhibitor, the method including the steps of:

(a) bringing a test material to be analyzed into contact with cells containing Beclin 1 protein; and (b) analyzing the degree of phosphorylation of the 30th amino acid residue serine of the Beclin 1 protein, wherein the test material is determined to be an autophagy activator if the phosphorylation of the Beclin 1 protein is up-regulated, and the test material is determined to be an autophagy inhibitor if the phosphorylation of the Beclin 1 protein is down-regulated.

The present inventors endeavored to develop a method for screening an autophagy activator or inhibitor capable of regulating autophagy that acts an important role in the maintenance of cellular homeostasis. As a result, the present inventors established that an autophagy activator or inhibitor could be screened by analyzing the degree of phosphorylation of the 30th amino acid residue serine of Beclin 1 protein.

The autophagy of the present invention is a system in which cells resupply intracellular nutrients by enclosing, in an environment that is deficient in intracellular nutrients, unnecessary proteins, aged small organs, and the like in membrane vacuoles composed of a lipid bilayer and then merging the same into lysosomes, thereby inducing the lysis of internal materials enclosed therein.

The method for screening an autophagy activator of the present invention will be described in detail by steps.

Step (a): Contact of Test Material

A test material to be analyzed is first brought into contact with cells containing Beclin 1 protein.

As the cells containing Beclin 1 protein, any animal cell known in the art may be used, and for example, 293T cells, HEK293T cells, mouse embryonic fibroblasts (MEF), or HeLa cells may be used.

As a medium that is usable to culture the animal cells, any medium that can be ordinarily used to culture animal cells may be used. For example, Eagles's MEM (Eagle's minimum essential medium, Eagle, H. *Science* 130:432(1959)), α-MEM (Stanner, C. P. et al., Nat. New Biol. 230:52(1971)), Iscove's MEM (Iscove, N. et al., *J. Exp. Med.* 147:923 (1978)), 199 medium (Morgan et al., *Proc. Soc. Exp. Bio. Med.*, 73:1(1950)), CMRL 1066, RPMI 1640 (Moore et al., J. Amer. Med. Assoc. 199:519(1967)), F12 (Ham, *Proc. Natl. Acad. Sci.* USA 53:288(1965)), F10 (Ham, R. G. Exp. Cell Res. 29:515(1963)), DMEM (Dulbecco's modification of Eagle's medium, Dulbecco, R. et al., *Virology* 8:396 (1959)), a mixture of DMEM and F12 (Barnes, D. et al., Anal. Biochem. 102:255(1980)), Way-mouth's MB752/1 (Waymouth, C. *J. Natl. Cancer Inst.* 22:1003(1959)), McCoy's 5A (McCoy, T. A., et al., *Proc. Soc. Exp. Biol. Med.* 100:115(1959)), and MCDB series (Ham, R. G. et al., *In Vitro* 14:11(1978)) may be used.

According to the method of the present invention, the test material to be analyzed is first brought into contact with cells containing Beclin 1 protein. As used herein to recite the screening method of the present invention, the term "test material" means an unknown material that is used in the screening in order to test whether the test material influences the phosphorylation of the 30th amino acid residue serine of Beclin 1 protein. The test material includes, but is not limited to, chemical materials, peptides, and natural extracts. The test material analyzed by the screening method of the present invention is a single compound or a mixture of compounds (e.g., a natural extract or a cell or tissue culture). The test material may be obtained from libraries of synthetic or natural compounds. The method of obtaining libraries of such compounds is known in the art. The libraries of synthetic compounds are commercially available from Maybridge Chemical Co. (UK), Comgenex (USA), Brandon Associates (USA), Microsource (USA), and Sigma-Aldrich (USA), and the libraries of natural compounds are commercially available from Pan Laboratories (USA) and MycoSearch (USA). The test material may be obtained through various known combinational library methods known in the art. For example, the test material may be obtained by a biological library method, a spatially-addressable parallel solid phase or solution phase library method, a synthetic library method requiring deconvolution, a "one-bead one-compound" library method, and a synthetic library method using affinity chromatography selection. The synthesis method for molecule library is disclosed in DeWitt et al., *Proc. Natl. Acad. Sci. U.S.A.* 90, 6909, 1993; Erb et al. *Proc. Natl. Acad. Sci. U.S.A.* 91, 11422, 1994; Zuckermann et al., *J. Med. Chem.* 37, 2678, 1994; Cho et al., *Science* 261, 1303, 1993; Carell et al., Angew. Chem. Int. Ed. Engl. 33, 2059, 1994; Carell et al., *Angew. Chem. Int. Ed. Engl.* 33, 2061; and Gallop et al., *J. Med. Chem.* 37, 1233, 1994.

Step (b): Analysis of Degree of Phosphorylation

The degree of phosphorylation of the 30th amino acid residue serine of Beclin 1 protein is analyzed. Here, the test material is determined to be an autophagy activator if the phosphorylation of the Beclin 1 protein is up-regulated, and the test material is determined to be an autophagy inhibitor if the phosphorylation of the Beclin 1 protein is down-regulated.

The autophagy activator may be used as a pharmaceutical composition for diagnosing or treating cancer or neurodegenerative diseases (see, EP 2383294).

As used herein, regarding the term "up-regulation", the phosphorylation of Beclin 1 protein is determined to be up-regulated if, on the basis of the inactivation of autophagy signaling (e.g., normal state of animal cells), the degree of phosphorylation of the 30th amino acid residue serine of Beclin 1 protein shows an increase pattern compared with a control treated without a test material.

As used herein, regarding the term "down-regulation", the phosphorylation of Beclin 1 protein is determined to be down-regulated if the degree of phosphorylation of the 30th amino acid residue serine of Beclin 1 protein shows a decrease pattern in a group treated with at least one selected from the group consisting of known autophagy inducing activators, such as amiodarone hydrochloride, Brefeldin A, carbamazepine, dexamethasone, dorsomorphin dihydrochloride, EB 1089 (vitamin D receptor agonist), GF 109203X (protein kinase C inhibitor), L-690,330 (inositol monophosphate inhibitor), NF 449 (P2X1 antagonist), niclosamide, nimodipine, nitrendipine, PI 103 hydrochloride (PI 3-kinase, mTOR and DNA-PK inhibitor), pifithrin-α hydrobromide, rapamycin, rottlerin, SMER 28, temozolomide, thapsigargin, torin, tunicamycin, valproic acid, and verapamil hydrochloride, compared with a control treated without a test material.

In order to analyze the degree of phosphorylation of the 30th amino acid residue serine of Beclin 1 protein, any phosphorylation analysis method known in the art may also be used. For example, western blot (Burnette WN. (1981). "Western blotting": electrophoretic transfer of proteins from sodium dodecyl sulfate-polyacrylamide gels to unmodified nitrocellulose and radiographic detection with antibody and radioiodinated protein A". Analytical Biochemistry 112 (2): 195-203), ELISA (Enzyme-Linked Immunosorbent Assay, Lequin R (2005). "Enzyme immunoassay (EIA)/enzyme-linked immunosorbent assay (ELISA)". Clin. Chem. 51 (12): 2415-8), and intracellular flow cytometry (www.abcam.com/?pageconfig=resource&rid=12060) may be used.

According to an embodiment of the present invention, the analyzing of the degree of phosphorylation of the 30th amino acid residue serine of the Beclin 1 protein may be performed using an antibody specifically binding to the Beclin 1 protein with the 30th amino acid residue serine phosphorylated. According to another embodiment of the present invention, the antibody specifically binding to the Beclin 1 protein with the 30th amino acid residue serine phosphorylated may be an antibody binding to an epitope composed of the amino acid sequence of SEQ ID NO: 1.

In accordance with another aspect of the present invention, there is provided a method for measuring the activity of autophagy, the method including bringing a sample into contact with the antibody specifically binding to Beclin 1 protein with the 30th amino acid residue serine phosphorylated.

As used herein, the term "sample" includes body fluids, such as tissue, blood, plasma, serum, urine, saliva, sweat, semen, or mucus, which are obtained from cultured cells, and eye, heart, intestine, kidney, liver, lung, muscle, spleen, or testis of an animal or human, but is not limited thereto.

In accordance with still another aspect of the present invention, there is provided a diagnostic kit for autophagy-related disease, including the antibody specifically binding to Beclin 1 protein with the 30th amino acid residue serine phosphorylated.

The autophagy-related disease includes neurodegenerative disease, autoimmune disease, cardiovascular disorder, metabolic disease, hamartoma tumor syndrome, genetic muscular disease, myopathy, or cancer.

In accordance with still another aspect of the present invention, there is provided an antibody specifically binding to Beclin 1 protein with the 30th amino acid residue serine phosphorylated.

As used herein, the term "antibody" is a specific antibody to Beclin 1 protein with the 30th amino acid residue serine phosphorylated, and includes the whole antibody form and an antigen binding fragment of the antibody molecule.

The whole antibody has a structure of two full-length light chains and two full-length heavy chains, and the light chain and heavy chain are linked via a disulfide bond. The heavy chain constant region has gamma (γ), mu (μ), alpha (α), delta (δ), and epsilon (ε) types, and gamma1 (γ1), gamma2 (γ2), gamma3 (γ3), gamma4 (γ4), alpha1 (α1), and alpha2 (α2) subclasses. The light chain constant region has kappa (κ) and lambda (λ) types (Cellular and Molecular Immunology, Wonsiewicz, M. J., Ed., Chapter 45, pp. 41-50, W. B. Saunders Co. Philadelphia, Pa.(1991); Nisonoff, A., Introduction to Molecular Immunology, 2nd Ed., Chapter 4, pp. 45-65, sinauer Associates, Inc., Sunderland, Mass. (1984)).

As used herein, the term "antigen binding fragment" refers to a fragment that retains an antigen binding function, and includes Fab, F(ab'), F(ab')2, and Fv. Out of the antibody fragments, Fab has variable regions of the light chain and the heavy chain, a constant region of the light chain, and a first constant region (CH1) of the heavy chain, and has one antigen binding site. Fab' is different from Fab in that the former has a hinge region including one or more cysteine residues at the C-terminal of the heavy chain CH1 domain. F(ab')2 antibody is formed through a disulfide bond between the cysteine residues at the hinge region of Fab'. Fv is a minimal antibody segment only having a heavy chain variable domain and a light chain variable domain, and a recombinant technique producing an Fv fragment is disclosed in WO 88/10649, WO 88/106630, WO 88/07085, WO 88/07086, and WO 88/09344. Two-chain Fv is linked by a non-covalent bond between one variable region of each heavy and light chain, and single-chain Fv is generally linked by a covalent bond via a peptide linker between one variable region of each heavy and light chain or is directly linked to each other at C-terminal, forming a dimer, such as two-chain Fv. These Fab fragments may be obtained using proteases (for example, the whole antibody is digested with papain to obtain Fab fragments, and is digested with pepsin to obtain F(ab')2 fragments), and may be prepared by a genetic recombinant technique.

The antibody of the present invention is a form of Fab or the whole antibody. In addition, the heavy chain constant region may be selected from any one isotype of gamma (γ), mu (μ), alpha (α), delta (δ), and epsilon (ε) types. The constant region preferably includes gamma1 (IgGI), gamma3 (IgG3), and gamma4 (IgG4) isotypes, and is most preferably gamma1 (IgGI) isotype. The light chain constant region may be κ or Δ isotype, and may preferably be κ isotype. Therefore, a preferable antibody of the present invention may have Fab or IgG1 type having κ light chain and γ1 heavy chain.

As used herein, the term "heavy chain" refers to the full-length heavy chain and fragments thereof, the full-length heavy chain including a variable domain VH that includes an amino acid sequence sufficient to impart specificity to an antigen, and three constant domains, CH1, CH2, and CH3. In addition, as used herein, the term "light chain" refers to the full-length light chain and fragments thereof, the full-length light chain including a variable domain VL that includes an amino acid sequence sufficient to impart specificity to an antigen, and a constant domain CL.

Beclin 1 protein antibody with the 30th amino acid residue phosphorylated or an antigen binding fragment thereof may include a variant of the amino acid sequence listed on the appended sequence listing within the range in which Beclin 1 protein with the 30th amino acid residue phosphorylated can be specifically recognized. For example, the amino acid sequence of the antibody may be varied to improve the binding affinity and/or other biological characteristics of the antibody. This variation includes, for example, deletion, insertion, and/or substitution with respect to amino acid residues of the antibody.

Such amino acid variations are provided on the basis of a relative similarity, e.g., hydrophobicity, hydrophilicity, charge, size, or the like of amino acid side chain substituents. By the analysis of size, shape, and type of the amino acid side chain substitutions, it can be seen that all of arginine, lysine, and histidine are positively charged residues; alanine, glycine, and serine have similar sizes; and phenylalanine, tryptophan, and tyrosine have similar shapes. Therefore, on the basis of these considerations, arginine, lysine, and histidine; alanine, glycine, and serine; and phenylalanine, tryptophan, and tyrosine may be considered to be biologically functional equivalents.

For introducing such variation, hydropathy indexes of amino acids may be considered. Each amino acid has been assigned a hydropathic index on the basis of its hydrophobicity and charge characteristics: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5)

The hydrophobic amino acid indexes are very important in giving interactive biological functions of proteins. It is well known that amino acids with similar hydrophobic indexes need to be substituted with each other to retain similar biological activities. In cases where variations are introduced with reference to the hydrophobic indexes, the substitution is made between amino acids having a hydrophobic index difference within preferably ±2, more preferably ±1, and still more preferably ±0.5.

Meanwhile, it is also well known that the substitution between amino acids with similar hydrophilicity values results in proteins having equivalent biological activity. As disclosed in U.S. Pat. No. 4,554,101, each amino acid residue has been assigned the following hydrophilicity values: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4)

In cases where the variations are introduced with reference to the hydrophilic indexes, the substitution is made between amino acids having a hydrophilicity value difference within preferably ±2, more preferably ±1, and still more preferably ±0.5.

The exchange of amino acid residues that does not substantially impair protein activity is well known to one skilled in the art (H. Neurath, R.L.Hill, The Proteins, Academic Press, New York, 1979). The most common substitutions are substitutions between amino acid residues Ala/

Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly.

Considering the foregoing variations having biological equivalent activity, the antibody or the nucleic acid molecule coding the antibody, of the present invention, is construed to also include sequences having substantial identity to the sequences set forth in the sequence listings. The substantial identity means that, when the sequence of the present invention and another optional sequence are aligned to correspond to each other as much as possible and the aligned sequences are analyzed using an algorithm that is commonly used in the art, the corresponding sequences have at least 61%, more preferably at least 70%, still more preferably at least 80%, and most preferably at least 90% sequence identity. Methods of alignment for sequence comparison are known in the art. various methods and algorithms for alignment are disclosed in Smith and Waterman, Adv. Appl. Math. 2:482(1981); Needleman and Wunsch, J. Mol. Bio. 48:443(1970); Pearson and Lipman, Methods in Mol. Biol. 24: 307-31(1988); Higgins and Sharp, Gene 73:237-44 (1988); Higgins and Sharp, CABIOS 5:151-3(1989); Corpet et al., Nuc. Acids Res. 16:10881-90(1988); Huang et al., Comp. Appl. BioSci. 8:155-65(1992), and Pearson et al., Meth. Mol. Biol. 24:307-31(1994). The NCBI Basic Local Alignment Search Tool (BLAST) (Altschul et al., J. Mol. Biol. 215:403-10(1990)) is accessible from NBCI (National Center for Biological Information), and on the internet, may be used in connection with sequence analysis programs, such as blastp, blasm, blastx, tblastn and tblastx. BLSAT may be accessed through www.ncbi.nlm.nih.gov/BLAST/. The sequence identity comparison method using such a program can be confirmed in www.ncbi.nlm.nih.gov/BLAST/blast_help. html.

According to an embodiment of the present invention, the antibody may be an antibody binding to an epitope composed of the amino acid sequence described by SEQ ID NO: 1.

The present invention provides a pharmaceutical composition for preventing or treating autophagy-related disease, the composition containing an autophagy activator as an active ingredient.

According to a preferable embodiment of the present invention, the composition of the present invention contains: (a) a pharmaceutically effective amount of the above-described autophagy activator of the present invention; and (b) a pharmaceutically acceptable carrier. As used herein, the term "pharmaceutically effective amount" refers to an amount sufficient to attain efficacy or activity of the foregoing autophagy activator.

In cases where the composition of the present invention is prepared as a pharmaceutical composition, the pharmaceutical composition of the present invention contains a pharmaceutically acceptable carrier. The pharmaceutically acceptable carrier contained in the pharmaceutical composition of the present invention is ordinarily used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further contain, in addition to the above ingredients, a lubricant, a wetting agent, a sweetening agent, a flavoring agent, an emulsifier, a suspending agent, a preservative, and the like. Suitable pharmaceutically acceptable carriers and agents are described in detail in Remington's Pharmaceutical Sciences (19th ed., 1995).

The pharmaceutical composition of the present invention may be administered orally or parenterally, and preferably, the oral administration manner is employed.

A suitable dose of the pharmaceutical composition of the present invention may vary depending on the factors, such as the method for formulation, the manner of administration, the age, body weight, gender, morbidity, and diet of the patient, time of administration, route of administration, excretion rate, and response sensitivity. The general dose of the pharmaceutical composition of the present invention is within the range of 0.001 µg/kg to 100 mg/kg in adults.

The pharmaceutical composition of the present invention may be formulated into a unit dosage form or may be prepared in a multi-dose container by using a pharmaceutically acceptable carrier and/or excipient according to the method easily conducted by a person having an ordinary skill in the art to which the present invention pertains. Here, the dosage form may be a solution in an oily or aqueous medium, a suspension, a syrup, or an emulsion, an extract, a pulvis, a powder, a granule, a tablet, or a capsule, and may further include a dispersant or a stabilizer.

The autophagy-related disease that can be prevented or treated by the pharmaceutical composition of the present invention is neurodegenerative disease, autoimmune disease, cardiovascular disorder, metabolic disease, hamartoma tumor syndrome, genetic muscular disease, myopathy, or cancer.

Herein, the neurodegenerative disease is selected from the group consisting of Alzheimer's disease, Parkinson's disease, Huntington's disease, and amyotrophic lateral sclerosis.

Examples of the autoimmune diseases may include alopecia areata, ankylosing spondylitis, antiphospholipid syndrome, autoimmune Addison's disease, autoimmune adrenal disease, autoimmune hemolytic anemia, autoimmune hepatitis, autoimmune ovaritis and testitis, autoimmune thrombocytopenia, Behcet's disease, bullous pemphigoid, cardiomyopathy, celiac sprue-dermatitis, chronic fatigue immune dysfunction syndrome, chronic inflammatory demyelinating polyradiculoneuropathy, Churg-Strauss syndrome, cicatricial pemphigoid, CREST syndrome, cold agglutinin disease, Crohn's disease, discoid lupus, essential mixed cryoglobulinemia, fibromyalgia-fibromyositis, glomerulonephritis, Grave's disease, Guillain-Barre syndrome, Hashimoto's thyroiditis, idiopathic pulmonary fibrosis, idiopathic thrombocytopenic purpuras, IgA nephropathy, juvenile arthritis, lichen planus, lupus erythematosus, Meniere's disease, mixed connective tissue disease, multiple sclerosis, type I or immune-mediated diabetes, myasthenia gravis, pemphigus vulgaris, pernicious anemia, polyarteritis nodosa, polychondritis, autoimmune polyglandular syndrome, polymyalgia rheumatica, polymyositis and dermatomyositis, primary agammaglobulinemia, primary biliary cirrhosis, psoriasis, psoriatic arthritis, Raynaud's phenomenon, Reiter's syndrome, rheumatoid arthritis, Sarcoidosis, scleroderma, stiff-person syndrome, systemic lupus erythematosus, lupus erythematosus, Takayasu's arteritis, temporal arteritis, giant cell arteritis, ulcerative colitis, uveitis, vitiligo and Wegener's granulomatosis.

The cardiovascular disorder is selected from the group consisting of coronary artery disease, cardiomyopathy, hypertensive heart disease, heart failure, corpulmonale, cardiac dysrhythmias, endocarditis, inflammatory cardiomegalia, myocarditis, valvular endocarditis, cerebrovascular disease, peripheral arterial disease, congenital heart disease, and rheumatic heart disease.

The metabolic disease is selected from the group consisting of obesity, diabetes, dyslipidemia, fatty liver, hypertension, artery hardening, hyperlipidemia, and hyperinsulinemia.

The cancer is selected from the group consisting of pituitary adenoma, glioma, brain tumor, epipharyngeal carcinoma, laryngeal cancer, thymic neoplasm, mesothelioma, breast cancer, lung cancer, stomach cancer, esophageal cancer, colorectal cancer, liver cancer, pancreatic cancer, pancreatic endocrine tumor, gallbladder cancer, penile carcinoma, ureteral cancer, renal cell carcinoma, prostate cancer, bladder cancer, non-Hodgkin's lymphoma, myelodysplastic syndrome, multiple myeloma, plasma cell tumor, leukemia, children cancer, skin cancer, ovarian cancer, and cervical cancer.

Advantageous Effects

Features and advantages of the present invention are summarized as follows:

(a) The present invention provides a method for screening an autophagy activator or inhibitor.

(b) The present invention first establishes a mechanism of phosphorylation of the 30th amino acid residue serine of Beclin 1 by ULK1.

(c) The present invention provides an antibody specifically binding to Beclin 1 protein with the 30th amino acid residue serine phosphorylated.

MODE FOR CARRYING OUT THE INVENTION

Figure 1A:
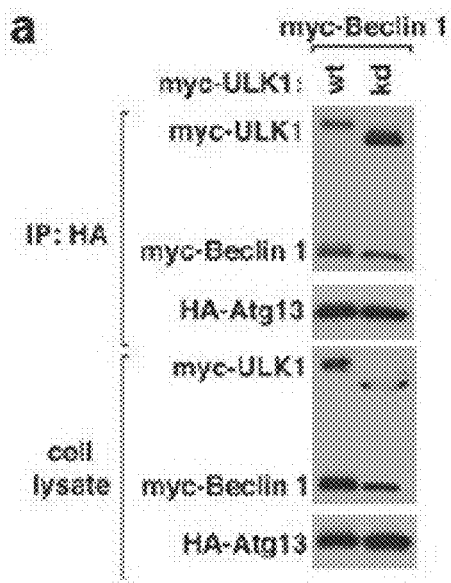
FIGS. 1a and 1b shows verification results of phosphorylation of Beclin 1 by ULK1.

Hereinafter, the present invention will be described in detail with reference to examples. These examples are only for illustrating the present invention more specifically, and it will be apparent to those skilled in the art that the scope of the present invention is not limited by these examples.

Examples

Materials and Methods
Chemicals and Antibodies

Anti-ULK1(sc-10900) and Beclin 1 (sc-11427 and sc-10086) antibodies were purchased from Santa Cruz Biotech. Anti-Atg14L antibodies were obtained from MBL (PD026) and Abgent (AP1832a). Anti-myc 9E10 was purchased from EMD Biosciences (OP10), and anti-HA antibody HA.11 was purchased from Covance (AFC-101P).

Plasmid Preparation and Mutagenesis

Human ULK1 and Atg13 cDNA clones were obtained from Katzusa laboratory. The kinase-dead mutant of ULK1, M92A was made by using the site-directed mutagenesis kit (Stratagene, CA). The cDNA for human Beclin 1 was purchased from Open Biosystems.

Cell Culture and Transfection

HEK293T, HeLa, and MEF cells were cultured in DMEM (Invitrogen, U.S.)_containing 10% fetal bovine serum (FBS), penicillin, and streptomycin under conditions of 37° C./5% $CO_2$. For transient expression, the cells were transfected with recombinant DNA using FuGENETM (Roche-diagnostics) according to the manufacturer's protocol. Cells were harvested 2 day after transfection, for co-immunoprecipitation.

Co-Immunoprecipitation and Western Blotting

For co-immunoprecipitation, cell extracts were prepared in a buffer containing 40 mM HEPES, pH 7.4, 120 mM NaCl, 1 mM EDTA, 50 mM NaF, 1.5 mM $Na_3VO_4$, 10 mM Mb-glycerophosphate, 1% triton X-100, and protease inhibitor (Roche). Immunoprecipitated proteins were washed four times with a lysis buffer, and loaded onto 8% Tris-glycine gels. The resultant proteins were transferred onto polyvinylidene difluoride (PVDF) membranes (Bio-Rad, USA), and detected with western blotting detection reagents (Perkin Elmer, USA).

Lentiviral Preparation

Lentiviral vector pLKO.1 coding shRNA targeting Atg14L or scramble sequences was transfected into HEK293T together with lentiviral packaging vectors pHR'8.2ΔR and pCMV-VSV-G using FuGENE 6. Viruses were collected 60 h after transfection, and HeLa cells were infected with the collected viruses in the presence of polybrene. The transfected cells were selected by puromycin treatment. The target sequences for Atg14L shRNA are 5'-CCATAGAACTTGGTCATGTTT-3' (SEQ ID NO:2) and 5'-CCACTTTCTTTCTATGGGATT-3' (SEQ ID NO:3), which are positioned at 3'-UTR. This shRNA does not target 3'-UTR-deficient recombinant Atg14L.

Immunostaining

HeLa or MEF cells were fixed in 4% formaldehyde (in PBS) for 15 min, and permeabilized using 0.3% Triton X-100 at room temperature for 30 min. The permeable cells were subjected to a constant-temperature reaction in PBS containing 1% bovine serum albumin (BSA) for 30 min, and then subjected to an antibody reaction at 4° C. overnight. Endogenous LC3 and Atg14L were stained using anti-LC antibodies (Novus, cat# NB100-2220 and Nanotools, cat#5F10) and anti-Atg14L antibody (MBL, PD026). Recombinant myc and HA-tagged proteins were monitored using Alexa647 fluorescent dye (Cell Signaling, cat#2233)-conjugated anti-myc antibody and anti-HA antibody (Covance, AFC-101P). After primary antibody binding, the cells were subjected to a constant-temperature reaction with Alexa Flour 488-conjugated anti-mouse IgG (Invitrogen, A-11001) and/or Alexa Flour 647-conjugated anti-rabbit IgG (Invitrogen, A-21443). The cells were stained with DAPI (4'-6-Diamidino-2-phenylindole, Invitrogen, D-1306). Images of the stained cells were obtained using Deltavision PersonelDV microscope (Applied Precision). The positioning of Atg14 wild type or S419A mutant of WIPI-1 or LC3 was statistically analyzed by student t-test using SigmaPlot 10.0 software (Systat Software, U.S.).

In Vivo Labeling

In order to determine the phosphorylation of Beclin 1 in living cells, myc-tagged ULK1 wild type and kinase-dead mutants were temporarily expressed in HEK293T cells. On day 2 after transfection, the reaction was performed in phosphate-free medium containing 10% diluted PBS for 4 h before the reaction for 1 h by adding 0.1 mCi[32P] orthophosphate (MPBiomedicals). For immunoprecipitation, myc-tagged ULK1 was isolated using anti-myc antibody. The isolated proteins were run on SDS-PAGE, and transferred to PVDF membrane, and an autoradiogram was obtained.

Results

Beclin 1 Phosphorylation Induction of ULK1

Figure 1B:
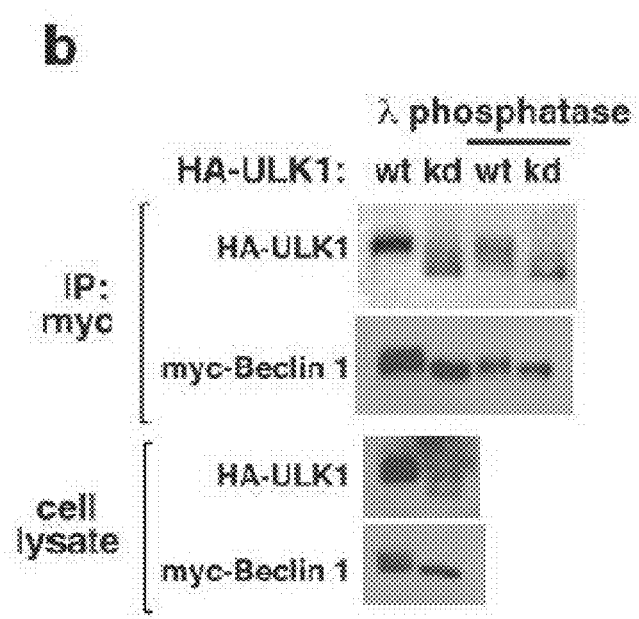

In 293 cells, myc-tagged Beclin 1 was co-expressed together with HA-tagged ULK1 wild type or M92A KD (kinase dead) mutant. Myc-Beclin 1 and HA-ULK1 were isolated by immunoprecipitation (IP) using anti-HA antibodies, and the shift aspect on SDS-PAGE was analyzed by western blot. It was confirmed that Beclin 1 and ULK1 or M92A KD mutant were conjugated to each other (FIG. 1a). Beclin 1 co-expressed together with ULK1 showed band shift, but Beclin 1 co-expressed together with ULK1 M92A KD showed no band shift. These results suggest the possibility of the Beclin 1 phosphorylation by the ULK1 wild type. 293T cells co-expressing myc-tagged Beclin 1 together with HA-tagged ULK1 wild type or M92A KD (kinase dead) were treated with/without lambda phosphatase, isolated through immunoprecipitation, and Co-IP was performed using anti-HA antibody, and the shift aspect on SDS-PAGE were analyzed by western blot. It showed that the phosphorylation of Beclin 1 shifted-up by ULK1 was isolated by phosphatase, indicating that ULK1 is a decisive clue in the phosphorylation of Beclin 1 (FIG. 1b).

Beclin 1 Phosphorylation

Figure 2:
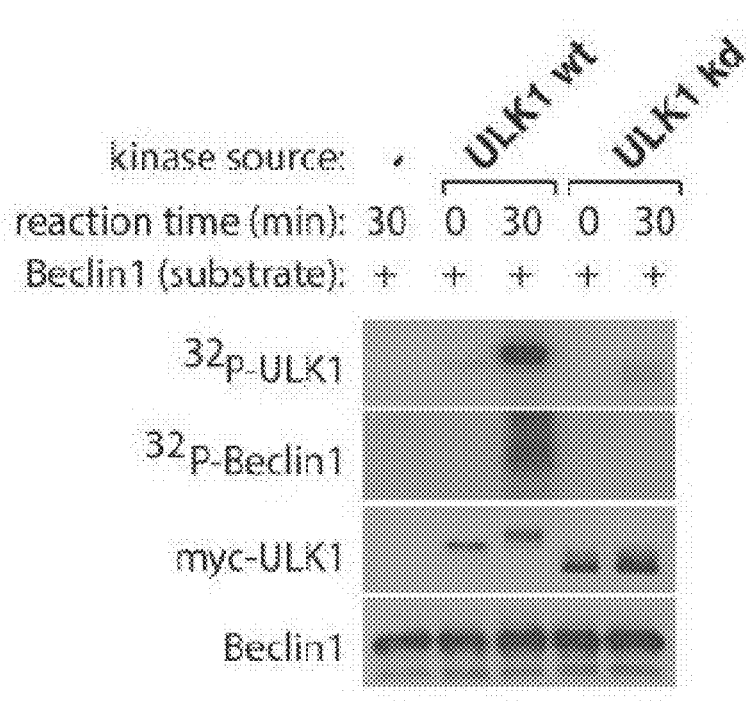
FIG. 2 shows verification results of direct phosphorylation of Beclin 1 by ULK1.

The overexpressed myc-tagged ULK1 wild type and KD (M92) mutant were isolated from HEK293T cells by immunoprecipitation (IP) using anti-myc antibody. Recombinant Beclin 1 was isolated from E. coli strain, and used as a substrate. Beclin 1 was subjected to constant-temperature reaction with ULK1 wild type or KD mutant isolated through immunoprecipitation at 37° C. in the presence of 32P-ATP. The incorporation of 32p into Beclin 1 and ULK1 was analyzed by autoradiogram. The levels of Myc-ULK1 and Beclin 1 were analyzed by western blot (FIG. 2). The ULK1 wild type phosphorylates Beclin 1, but KD mutant-added Beclin 1 was not phosphorylated. That is, the results show that the kinase activity of ULK1 is important in the phosphorylation of Beclin 1.

Beclin 1 Ser30 Epitope

HA-tagged Beclin 1 and myc-tagged ULK1 wild type or KD mutant were expressed and immunoprecipitation was performed using HA antibody. The bands shown on SDS-PAGE were respectively extracted, and the phosphorylation sites of ULK1 were analyzed through LC-MS assay. As an analysis result, Ser30 of Beclin 1 was analyzed as a site with high possibility. In order to develop antibodies specifically binding to Beclin 1 protein with the amino acid residue serine phosphorylated, the epitope of antibody was synthesized as follows. The following synthetic peptide is in a form in which the fifth amino acid residue serine is phosphorylated.

Cysteine (cys) at the N-terminal was arbitrarily added for conjugation to the carrier protein. The epitopes were synthesized to construct antibodies against Ser30 phosphorylation of Beclin 1.www.abfrontier. com/cs/antibodyPoly.do).

Beclin 1 Ser30 Phosphorylation

Figure 3:
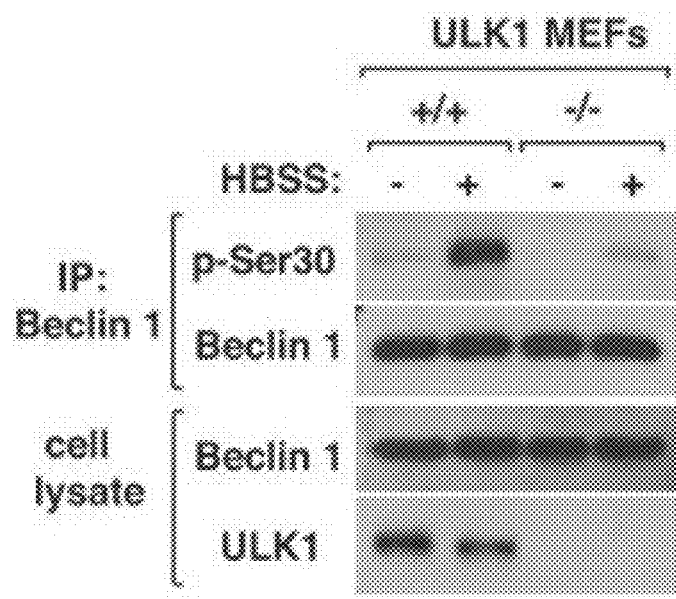
FIG. 3 shows verification results of Ser30 phosphorylation of Beclin 1 by ULK1.

ULK1+/+ MEF and ULK1−/− MEF were cultured in HBSS media for 2 h. Endogenous Beclin 1 was isolated by immunoprecipitation. The phosphorylation of Ser30 was analyzed using antibodies developed by the present inventors (FIG. 3). The kinase activity of ULK1 was increased in HBSS media, and here, it was estimated that the activated ULK1 would phosphorylate the 30th amino acid residue serine of Beclin 1. As a test result, the self-developed Beclin 1 Ser30 antibody performed a selective reaction on the phosphorylation sites of Beclin 1 phosphorylated by ULK1.

Beclin 1 Ser30 Phosphorylation at Starvation

Figure 4:
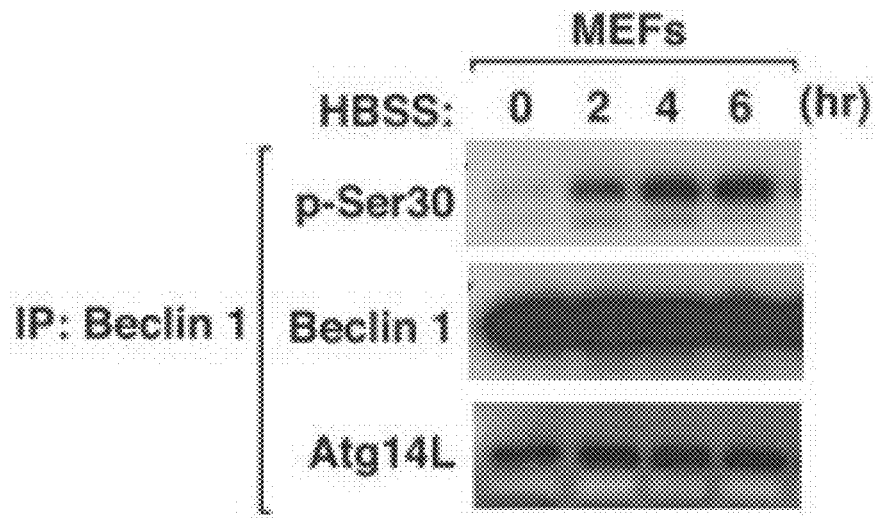
FIG. 4 shows verification results of Ser30 phosphorylation of Beclin 1 at starvation state.

MEF cells were cultured in HBSS for predetermined periods of time (0, 2, 4, and 6 h). Endogenous Beclin 1 was isolated by immunoprecipitation. The phosphorylation of Ser30 was analyzed using rabbit antibodies developed in the present invention. It was verified that Ser30 of Beclin 1 was phosphorylated at starvation state (FIG. 4).

Beclin 1 Ser30 Phosphorylation by Rapamycin

Figure 5:
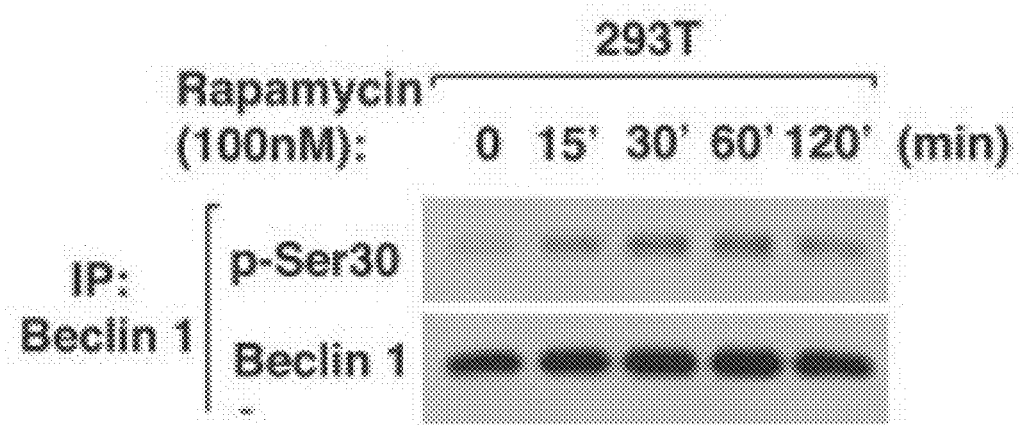
FIG. 5 shows verification results of Ser30 phosphorylation of Beclin 1 by rapamycin treatment.

HEK293T cells were treated with rapamycin for predetermined periods of time (0, 15, 30, 60, and 120 min). Endogenous Beclin 1 was isolated by immunoprecipitation. The phosphorylation of Ser30 was analyzed using rabbit antibodies developed in the present invention. It was verified that Ser30 of Beclin 1 was phosphorylated by rapamycin (FIG. 5). Rapamycin increases the activity of ULK1.

Beclin 1 Ser30 Phosphorylation by Torin

Figure 6:
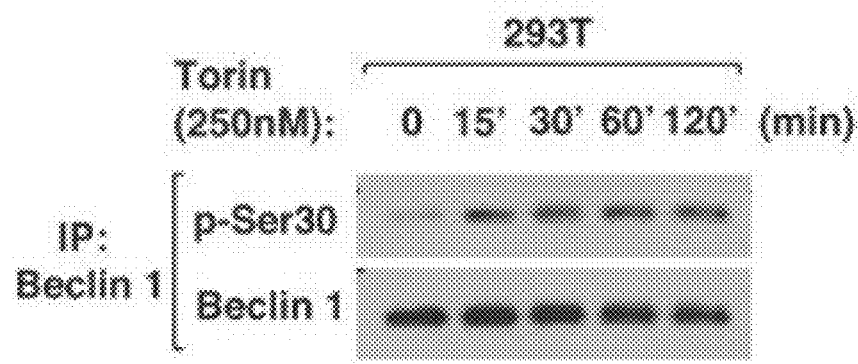
FIG. 6 shows verification results of Ser30 phosphorylation of Beclin 1 by torin treatment.

HEK293T cells were treated with torin for predetermined periods of time (0, 15, 30, 60, and 120 min). Endogenous Beclin 1 was isolated by immunoprecipitation. The phosphorylation of Ser30 was analyzed using rabbit antibodies developed in the present invention. It was verified that Ser30 of Beclin 1 was phosphorylated by torin (FIG. 6).

Autophagy Activation

Figure 7:
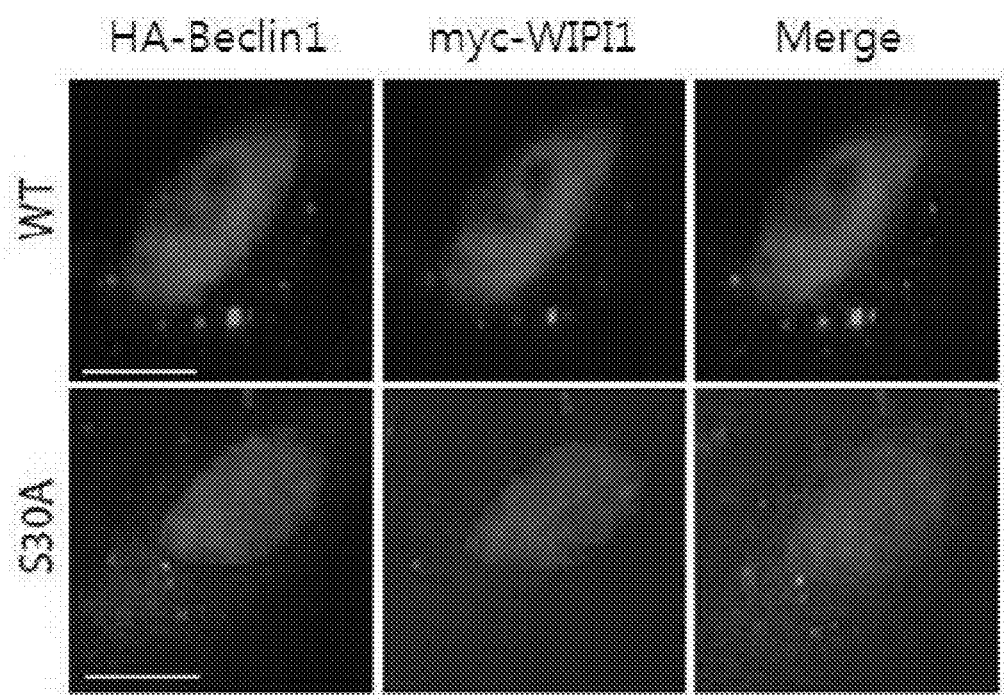
FIG. 7 shows the importance of Ser30 phosphorylation of Beclin 1 on autophagy activation.

In Beclin 1-silent HeLa cells, myc-tagged WIPI-1 and HA-tagged Beclin 1 wild type or S30A mutant were temporally expressed. The cells were treated with rapamycin for 1 h, and then immunostained with HA-Beclin 1 (green) and myc-WIPI1 (red). The nucleus (blue) were stained with DAPI. Beclin 1 puncta and WIPI-1 co-location was analyzed (FIG. 7). It was verified that the mutation of the 30th amino acid residue serine of Beclin 1 decreased the autophagy activity.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. An isolated antibody that specifically binds to phosphorylated Beclin 1, said antibody binds to the epitope of the amino acid sequence set forth in SEQ ID NO:1, wherein the fifth amino acid residue serine is phosphorylated.

2. A kit comprising the antibody of claim 1.

3. A composition comprising the antibody of claim 1.

4. The composition of claim 3, wherein the composition is a pharmaceutical composition comprising a pharmaceutically effective amount of the antibody.

5. The composition of claim 4, further comprising one or more pharmaceutically acceptable carriers.

* * * * *

SEQUENCE LISTING

<160> NUMBER OF SEQ ID NOS: 3

<210> SEQ ID NO 1
<211> LENGTH: 11
<212> TYPE: PRT
<213> ORGANISM: Artificial Sequence

```
<220> FEATURE:
<223> OTHER INFORMATION: Epitope for phosphorylation of Beclin1 Ser30

<400> SEQUENCE: 1

Lys Leu Asp Thr Ser Phe Lys Ile Leu Asp Arg
1               5                   10

<210> SEQ ID NO 2
<211> LENGTH: 21
<212> TYPE: DNA
<213> ORGANISM: Artificial Sequence
<220> FEATURE:
<223> OTHER INFORMATION: Atg14L shRNA target sequence

<400> SEQUENCE: 2
ccatagaact tggtcatgtt t                                          21

<210> SEQ ID NO 3
<211> LENGTH: 21
<212> TYPE: DNA
<213> ORGANISM: Artificial Sequence
<220> FEATURE:
<223> OTHER INFORMATION: Atg14L shRNA target sequence

<400> SEQUENCE: 3
ccactttctt tctatgggat t                                          21
```